(12) United States Patent
Takahashi et al.

(10) Patent No.: US 6,211,411 B1
(45) Date of Patent: Apr. 3, 2001

(54) PROCESS FOR PRODUCING RETINAL AND INTERMEDIATE FOR PRODUCING THE SAME

(75) Inventors: Toshiya Takahashi, Ibaraki; Naoto Konya, Takatsuki; Shinzo Seko, Toyonaka, all of (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/328,895

(22) Filed: Jun. 9, 1999

(30) Foreign Application Priority Data

Jun. 12, 1998 (JP) .................................. 10-165362

(51) Int. Cl.$^7$ .................................. C07C 315/04
(52) U.S. Cl. .................. 568/31; 568/32; 568/34; 568/447; 568/446
(58) Field of Search ........................ 568/446, 447, 568/28, 31, 32, 34

(56) References Cited

U.S. PATENT DOCUMENTS

| | | | |
|---|---|---|---|
| 4,175,205 | * 11/1979 | Decor | 560/260 |
| 4,825,006 | * 4/1989 | Otera et al. | 568/32 |
| 5,087,762 | 2/1992 | Mori et al. | 568/447 |
| 5,118,866 | 6/1992 | Knaus et al. | 568/447 |
| 5,185,468 | * 2/1993 | Mori et al. | 568/31 |
| 5,237,102 | * 8/1993 | Mori et al. | 568/31 |
| 5,449,836 | * 9/1995 | Chabardes | 568/594 |

OTHER PUBLICATIONS

CA:119:203649 abs of Bull Soc Chim Fr by Chemla et al vol. 130(2) pp 200–5, Feb. 1993.*

Chemla et al, A Stereoselective $C_{10}+C_{10}$ Route to Retinal, Bull. Soc. Chim. Fr, pp. 200–205, 1993.

Solladie et al, Synthesis of New Aromatic Retinoid Analogues by Low–Valent Titanium Induced Reductive Elimination, J. Org. Chem., vol. 54, No. 11, pp. 2620–2628, 1989.

E.G.E. Hawkins et al., "Vitamin–A Aldehyde (Axerophthal)", *J. Chem. Soc.*, 1944, p. 411.

von P. Karrer et al., "Über die katalytische Oxydation von Vitamin A mit Sauerstoff und Platin zu Vitamin–A–aldehyd (eine neue Methode)", *Helv. Chem., Acta*, vol. 40, 1957, pp. 265–266.

Hugues Bienaymé, "Efficiency of Organometallic Catalysis in a New "Ecological" Synthesis of Retinal", *Tetrahedron Letters,*, vol. 35, No. 40, 1994, pp. 7383–7386.

Teruaki Mukaiyama et al., "A New Synthesis of Vitamin A", *Chemistry Letters*, Chemical Society of Japan, 1975, pp. 1201–1202.

* cited by examiner

*Primary Examiner*—Jean F. Vollano
(74) *Attorney, Agent, or Firm*—Sughrue, Mion, Zinn, Macpeak & Seas, PLLC

(57) ABSTRACT

There are disclosed sulfone aldehyde derivatives of the Formula (1):

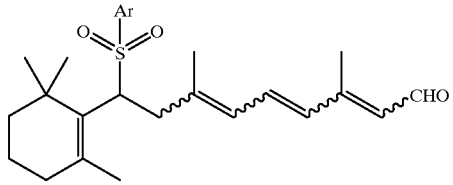

(1)

wherein Ar is an optionally substituted aryl group, a process for producing retinal by using the same, and an intermediate for producing the sulfone aldehyde derivative.

22 Claims, No Drawings

PROCESS FOR PRODUCING RETINAL AND INTERMEDIATE FOR PRODUCING THE SAME

DETAILED DESCRIPTION OF THE INVENTION

1. Field of the Invention

The present invention relates to a process for producing retinal, a key material for producing a carotenoid that is an important ingredient of pharmaceuticals, food and feed additives, and an intermediate for producing the same.

2. Description of the Related Art

Retinal is an important material for producing carotenoid such as β-carotene and a process has been known for producing the same by oxidizing retinol. However, the process has a drawback in that the process requires the use of retinol, which is very unstable to heat, light and oxygen. (e.g., J.Chem. Soc. 411 (1944), JP 63-233943A, Helv. Chim. Acta 40, 265 (1957), JP7-103095B).

There has also been known a carbon-increment reaction process at the side chain of C13 compounds such as β-ionone (e.g., Tetrahedron Lett. 35, 7383 (1994)), or C10 compound citral (Chem. Lett. 1201 (1975)). These processes are not always advantageous from an industrial view point because commercially expensive β-ionone or citral, which are produced by multistep processes, is required.

SUMMARY OF THE INVENTION

An object of the present invention is to provide a process for producing retinal by using a novel intermediate which is easy to handle and readily available from a sulfone derivative of the formula (6) which is obtained from inexpensive materials as depicted in Scheme 1 below by using a coupling reaction of a C10 allyl halide derivative (5) with a C10-cyclic sulfone derivative (4) which can be derivatized from a rather inexpensive C10 compound such as linalool or geraniol or the like, such that a new synthetic process to retinal without using unstable retinol is completed.

Scheme 1

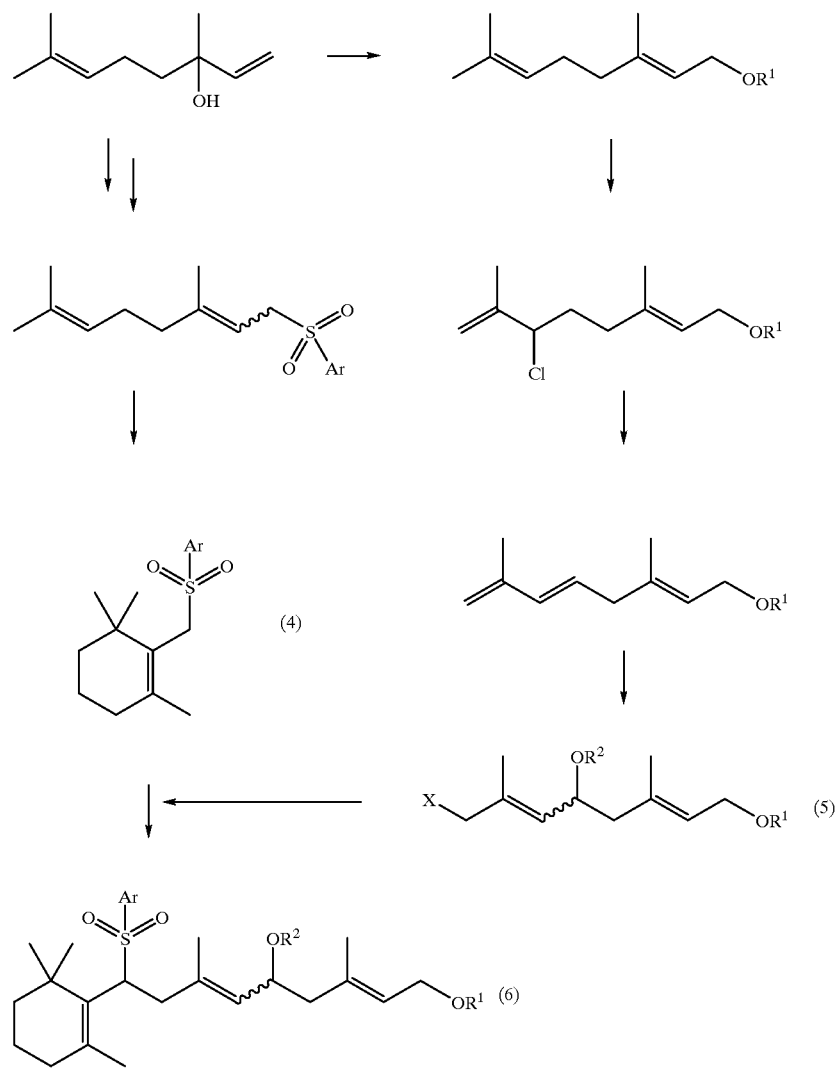

DESCRIPTION OF THE PREFERRED EMBODIMENTS

The present invention provides:

1. A sulfone aldehyde derivative of the Formula (1):

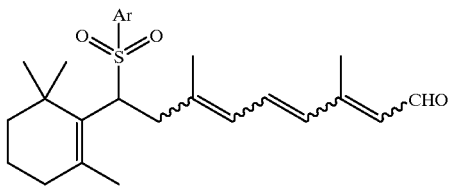

(1)

wherein Ar is an optionally substituted aryl group;

2. A method for producing a sulfone aldehyde derivative of the Formula (1) as defined above, which comprises subjecting a sulfone derivative of the Formula (2):

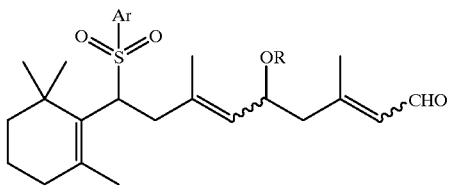

(2)

wherein Ar is an optionally substituted aryl group, and R is a hydrogen atom or a protective group for a hydroxy group, to an elimination reaction, whereby eliminating the OR group;

3. A sulfone derivative of the Formula (2) as defined above,

4. A method for producing a sulfone derivative of the Formula (2) as defined above, which comprises oxidizing a hydroxysulfone derivative of the Formula (3):

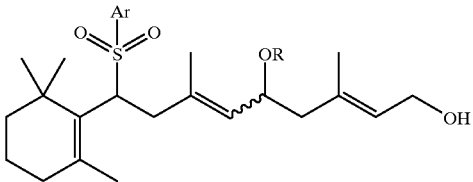

(3)

wherein Ar and R are the same as defined above; and

5. A method for producing retinal, which comprises contacting the sulfone aldehyde derivative of the Formula (1) as defined above with a base.

First, explanation will be made to the definitions of R and Ar in the chemical formulae (1), (2) and (3) of the present specification.

R represents a hydrogen atom or a protective group for a hydroxyl group. Examples of the protective group include:
an acyl group such as acetyl, pivaloyl, benzoyl, p-nitrobenzoyl and the like,
a silyl group such as trimethylsilyl, t-butyldimethylsilyl, t-butyldiphenylsilyl and the like,
a tetrahydropyranyl group, alkoxymethyl group such as methoxymethyl, methoxyethoxymethyl, 1-ethoxyethyl and the like,
a benzyl group, p-methoxybenzyl group, t-butyl group, trityl group, 2,2,2-trichloroethoxycarbonyl group, an allyloxycarbonyl group and the like.

Ar represents an optionally substituted aryl group. Examples of the aryl group includes phenyl group, naphthyl group and the like, and the substituent includes:
a C1–C5 alkyl group (e.g., a methyl, ethyl, n-propyl, i-propyl, n-butyl, s-butyl, i-butyl, t-butyl, n-pentyl, neo-pentyl group, and the like),
a C1–C5 alkoxy group (e.g., a methoxy, ethoxy, n-propoxy, i-propoxy, n-butoxy, s-butoxy, i-butoxy, t-butoxy, n-pentyloxy, neo-pentyloxy group, and the like),
a halogen atom (e.g., a chlorine, bromine, fluorine or iodine atom), a nitro group and the like.

Specific examples thereof include phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl, p-nitrophenyl and the like.

The sulfone aldehyde derivative of the Formula (1) above can be produced by a method which comprises subjecting the sulfone derivative of the Formula (2) to an elimination reaction, whereby the OR group is eliminated.

When R in the sulfone derivative (2) is a hydrogen atom, the elimination reaction to produce the sulfone aldehyde derivative (1) is usually effected by subjecting the sulfone derivative (2) to a dehydration reaction in the presence of an acid catalyst.

The acid catalyst employed in this reaction includes a Lewis acid, a Brønsted acid, a heteropolyacid, an acidic ion exchange resin, an acid chloride and the like. Examples of the Lewis acid include zinc chloride, boron trifluoride ether complex and a triflate of a rare earth element such as scandium triflate, and examples of a Brønsted acid include hydrobromic acid, hydrochloric acid, sulfuric acid, sulfonic acid, triphenylphosphine hydrobromide, pyridine hydrochloride and benzoic acid, and the acidic ion exchange resin may be a strongly acidic resin having a terminal sulfonate group.

Examples of the acid chloride include thionyl chloride, phosphorus oxychloride and the like.

The amount of an acid catalyst is usually 0.1 to 1 molar equivalent, alternatively 0.1 to 1 part by weight based on a sulfone derivative (2).

The reaction described above usually employs an organic solvent including a hydrocarbon solvent such as n-hexane, n-heptane, cyclohexane, n-pentane, toluene, xylene and the like, an ether solvent such as 1,4-dioxane, diethylether, tetrahydrofuran, anisol and the like, a halogenated solvent such as chloroform, dichloromethane, 1,2-dichloroethane, monochlorobenzene, o-dichlorobenzene and the like, an aprotic polar solvent such as N,N-dimethylformamide, dimethylsulfoxide, N,N-dimethylacetamide, hexamethylphosphoric triamide and the like.

The reaction temperature usually ranges from −78° C. to the boiling point of the solvent employed, and preferably from −10° C. to 60° C. The reaction time may vary depending on the types of the catalyst and the temperature employed in the reaction, and usually ranges from 1 hour to 24 hours.

After the reaction, the sulfone aldehyde derivative (1) is usually isolated by a conventional post treatment such as extraction, evaporation, and/or recrystallization, and may be further purified by chromatography on a silica gel, if necessary.

When R in the sulfone derivative (2) is a protective group for a hydroxyl group, then the sulfone aldehyde derivative (1) can be obtained by an elimination reaction in the presence of a palladium catalyst, whereby the OR is removed. The reaction is usually effected, for example, by a method which comprises contacting the sulfone derivative (2) with a palladium catalyst.

Examples of the palladium catalyst employed in the reaction described above include tetrakis(triphenylphosphine)palladium, palladium acetate, palladium propionate, dichlorobis(triphenylphosphine)palladium, di-p-chlorobis(η-allyl)palladium, dichloro(η-1,5-cyclooctadiene)palladium, dichloro(η-2,5-norbornadiene)palladium, dichlorobis(acetonitrile)palladium, dichlorobis(benzonitrile)palladium, dichlorobis(N,N-dimethylformamide)palladium, bis(acethylacetonato)palladium, bis(dimethylglyoxymato)palladium and the like. When a divalent palladium catalyst is employed, it is preferred to use a phosphine together.

The amounts of the catalyst and a phosphine to be used is usually 1 to 10 molar % based on the sulfone derivative of the Formula (2).

The reaction described above usually employs an organic solvent including an ether solvent such as 1,4-dioxane, tetrahydrofuran and the like, a hydrocarbon solvent such as n-hexane, n-heptane, cyclohexane, n-pentane, toluene, xylene and the like, a halogenated solvent such as chloroform, dichloromethane, 1,2-dichloroethane, monochlorobenzene, o-dichlorobenzene and the like, an aprotic polar solvent such as N,N-dimethylformamide, dimethylsulfoxide, N,N-dimethylacetamide, hexamethylphosphoric triamide and the like.

The reaction temperature usually ranges from −30° C. to the boiling point of the solvent employed, and preferably from 30° C. to 80° C. The reaction time may vary depending on the types of the catalyst and the temperature employed in the reaction, and usually ranges from 1 hour to 24 hours. After the reaction, the sulfone aldehyde derivative (1) is usually isolated by a conventional post treatment, such as extraction, and evaporation, and may be further purified by chromatography on a silica gel, if necessary.

The sulfone derivative (2) can be obtained by a method which comprises oxidizing the hydroxysulfone derivative of the Formula (3). The oxidation reaction employs an oxidizing reagent including a salt or an oxide of a metal such as chromium and manganese and an oxide of selenium, for example, pyridinium chlorochromate, pyridinium dichromate, manganese dioxide, selenium dioxide and the like. The amount of the reagent to be used is usually 1 to 10 molar equivalents, preferably 1 to 3 molar equivalents based on the hydroxysulfone derivative (3).

The reaction described above usually employs an organic solvent including a hydrocarbon solvent such as n-hexane, n-heptane, cyclohexane, n-pentane, toluene, xylene and the like, a halogenated solvent such as chloroform, dichloromethane, 1,2-dichloroethane, monochlorobenzene, o-dichlorobenzene and the like, an aprotic polar solvent such as N,N-dimethylformamide, dimethylsulfoxide, N,N-dimethylacetamide, hexamethylphosphoric triamide and the like, and an ether such as 1,4-dioxane, tetrahydrofuran and the like.

The reaction temperature usually ranges from 0° C. to the boiling point of the solvent employed. The reaction time may vary depending on the types of the oxidizing reagent and the temperature employed in the reaction, and usually ranges from 1 hour to 24 hours.

After the reaction, the sulfone derivative (2) can be obtained by a conventional post treatment such as extraction, and evaporation, and may be further purified by chromatography on a silica gel, if necessary.

Specific examples of the sulfone derivative of the Formula (2) include following compounds in Table 1 below.

TABLE 1

| No. | Ar | R |
|---|---|---|
| 1 | Phenyl | H |
| 2 | naphthyl | H |
| 3 | o-tolyl | H |
| 4 | m-tolyl | H |
| 5 | p-tolyl | H |
| 6 | o-methoxyphenyl | H |
| 7 | m-methoxyphenyl | H |
| 8 | p-methoxyphenyl | H |
| 9 | o-chlorophenyl | H |
| 10 | m-chlorophenyl | H |
| 11 | p-chlorophenyl | H |
| 12 | o-bromophenyl | H |
| 13 | m-bromophenyl | H |
| 14 | p-bromophenyl | H |
| 15 | o-iodophenyl | H |
| 16 | m-iodophenyl | H |
| 17 | p-iodophenyl | H |
| 18 | o-fluorophenyl | H |
| 19 | m-fluorophenyl | H |
| 20 | p-fluorophenyl | H |
| 21 | o-nitrophenyl | H |
| 22 | m-nitrophenyl | H |
| 23 | p-nitrophenyl | H |
| 24 | phenyl | Acetyl |
| 25 | naphthyl | Acetyl |
| 26 | o-tolyl | Acetyl |
| 27 | m-tolyl | Acetyl |
| 28 | p-tolyl | Acetyl |
| 29 | o-methoxyphenyl | Acetyl |
| 30 | m-methoxyphenyl | Acetyl |
| 31 | p-methoxyphenyl | Acetyl |
| 32 | o-chlorophenyl | Acetyl |
| 33 | m-chlorophenyl | Acetyl |
| 34 | p-chlorophenyl | Acetyl |
| 35 | o-bromophenyl | Acetyl |
| 36 | m-bromophenyl | Acetyl |
| 37 | p-bromophenyl | Acetyl |
| 38 | o-iodophenyl | Acetyl |
| 39 | m-iodophenyl | Acetyl |
| 40 | p-iodophenyl | Acetyl |
| 41 | o-fluorophenyl | Acetyl |
| 42 | m-fluorophenyl | Acetyl |
| 43 | p-fluorophenyl | Acetyl |
| 44 | o-nitrophenyl | Acetyl |
| 45 | m-nitrophenyl | Acetyl |
| 46 | p-nitrophenyl | Acetyl |

Specific examples of the sulfone derivative of the Formula (2) further include those compounds in which the hydrogen atom or the acetyl group for R group in the above described compounds is replaced by a group selected from pivaloyl, benzoyl, p-nitrobenzoyl, trimethylsilyl, t-butyldimethylsilyl, t-butyldiphenylsilyl, tetrahydropyranyl, methoxymethyl, methoxyethoxymethyl, 1-ethoxyethyl, benzyl, p-methoxybenzyl, t-butyl, trityl, 2,2,2-trichloroethoxycarbonyl, allyloxycarbonyl group.

The sulfone aldehyde derivative (1) can be derivatized to retinal. Thus, retinal can be produced by a method which comprises contacting the sulfone aldehyde derivative of the Formula (1) with a base.

Examples of the base to be used preferably include a bicyclic tertiary amine compound such as DBU (1,8-Diazabicyclo[5.4.0]undec-7-ene) and DBN (1,5-Diazabicyclo[4.3.0]non-5-ene). The amount of the amine is usually 0.1 mole to 3 moles per mole of the sulfone aldehyde derivative of the Formula (1). Alternatively, the above-described base may be used in catalytic amount together with one equivalent or more of an alkali metal carbonate such as potassium carbonate or sodium carbonate.

The reaction of the sulfone aldehyde derivative (1) with the base is usually conducted by using an organic solvent.

Examples of the solvent include an ether such as 1,4-dioxane, tetrahydrofuran and the like, a hydrocarbon solvent such as n-hexane, n-heptane, cyclohexane, n-pentane, toluene, xylene and the like, a halogenated solvent such as chloroform, dichloromethane, 1,2-dichloroethane, monochlorobenzene, o-dichlorobenzene and the like, an aprotic polar solvent such as acetonitrile, N,N-dimethylformamide, dimethylsulfoxide, N,N-dimethylacetamide, hexamethylphosphoric triamide and the like.

The reaction temperature usually ranges from −30° C. to the boiling point of the solvent employed, preferably 20° C. to 100° C. The reaction time may vary depending on the types of the oxidizing reagent and the temperature employed in the reaction, and usually ranges from 1 hour to 24 hours.

After completion of the reaction, retinal is usually isolated by a conventional post treatment such as extraction, and evaporation, and may be further purified by chromatography on a silica gel, if necessary.

The sulfone derivative (6)

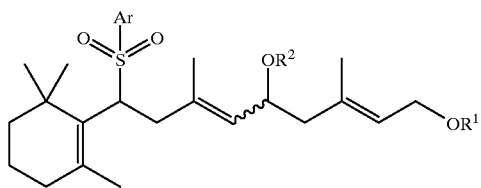

(6)

wherein $R^1$ and $R^2$ independently represent a protective group for a hydroxyl group can be produced by a method which comprises reacting a sulfone of the Formula (4):

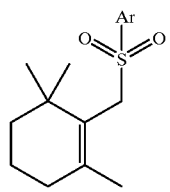

(4)

wherein Ar is defined as above, with an allyl halide derivative of the Formula (5):

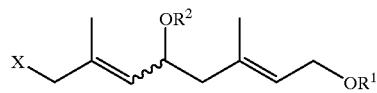

(5)

wherein X is a halogen atom and $R^1$ and $R^2$ are the same as defined above, in the presence of a base. The sulfone derivative (6) can be further deprotected by a conventional method to produce the hydroxysulfone derivative of the Formula (3).

The protective group for a hydroxyl group for $R_1$ in the allyl halide derivative of the Formula (5) may, for example, be a hydroxyl protective group similar to those exemplified above for R.

The halogen atom for X in the allyl halide derivative (5) may be a chlorine atom, a bromine atom, an iodine atom and the like.

The base employed in the reaction described above includes an alkyllithium, a Grignard reagent, an alkali metal hydroxide, an alkali earth metal hydroxide, an alkali metal hydride, an alkali earth metal hydride, an alkali metal alkoxide, an alkali earth metal alkoxide, and typical examples are n-butyllithium, s-butyllithium, t-butyllithium, ethyl magnesium bromide, ethyl magnesium chloride, sodium hydroxide, potassium hydroxide, sodium hydride, potassium hydride, sodium methoxide, potassium methoxide, potassium t-butoxide, sodium t-butoxide and the like. The amount of such base to be employed is usually 0.1 to 2 molar equivalents based on the sulfone (4).

In the reaction described above, a phase transfer catalyst may be employed, depending on the base used.

The phase transfer catalyst to be employed may be a quaternary ammonium salt, a quaternary phosphonium salt, a sulfonium salt and the like.

The quaternary ammonium salt includes tetramethylammonium chloride, tetraethylammonium chloride, tetrapropylammonium chloride, tetrabutylammonium chloride, tetrapentylammonium chloride, tetrahexylammonium chloride, tetraheptylammonium chloride, tetraoctylammonium chloride, tetrahexadecylammonium chloride, tetraoctadecylammonium chloride, benzyltrimethylammonium chloride, benzyltriethylammonium chloride, benzyltributylammonium chloride, 1-methylpyridinium chloride, 1-hexadecylpyridinium chloride, 1,4-dimethylpyridinium chloride, trimethylcyclopropylammonium chloride, tetramethylammonium bromide, tetraethylammonium bromide, tetrapropylammonium bromide, tetrabutylammonium bromide, tetrapentylammonium bromide, tetrahexylammonium bromide, tetraheptylammonium bromide, tetraoctylammonium bromide, tetrahexadecylammonium bromide, tetraoctadecylammonium bromide, benzyltrimethylammonium bromide, benzyltriethylammonium bromide, benzyltributylammonium bromide, 1-methylpyridinium bromide, 1-hexadecylpyridinium bromide, 1,4-dimethylpyridinium bromide, trimethylcyclopropylammonium bromide, tetramethylammonium iodide, tetrabutylammonium iodide, tetraoctylammonium iodide, t-butylethyldimethylammonium iodide, tetradecyltrimethylammonium iodide, hexadecyltrimethylammonium iodide, octadecyltrimethylammonium iodide, benzyltrimethylammonium iodide, benzyltriethylammonium iodide, benzyltributylammonium iodide and the like.

The quaternery phosphonium salt includes tributylmethylphosphonium chloride, triethylmethylphosphonium chloride, methyltriphenoxyphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride, hexadecyldimethylethylphosphonium chloride, tetraphenylphosphonium chloride, tributylmethylphosphonium bromide, triethylmethylphosphonium bromide, methyltriphenoxyphosphonium bromide, butyltriphenylphosphonium bromide, tetrabutylphosphonium bromide, benzyltriphenylphosphonium bromide, hexadecyltrimethylphosphonium bromide, hexadecyltributylphosphonium bromide, hexadecyldimethylethylphosphonium bromide, tetraphenylphosphonium bromide, tributylmethylphosphonium iodide, triethylmethylphosphonium iodide, methyltriphenoxyphosphonium iodide, butyltriphenylphosphonium iodide, tetrabutylphosphonium iodide, benyltriphenylphosphonium iodide, hexadecyltrimethylphosphonium iodide and the like.

The sulfonium salt includes dibutylmethylsulfonium chloride, trimethylsulfonium chloride, triethylsulfonium chloride, dibutylmethylsulfonium bromide, trimethylsulfonium bromide, triethylsulfonium bromide, dibutylmethylsulfonium iodide, trimethylsulfonium iodide, triethylsulfonium iodide, and the like.

The amount of the phase transfer catalyst to be used is usually 0.01 to 0.2 molar equivalent based on a sulfone (4), preferably 0.02 to 0.1 molar equivalent.

The reaction described above usually employs an organic solvent including an ether solvent such as diethylether, tetrahydrofuran, anisol and the like, a hydrocarbon solvent such as n-hexane, n-heptane, cyclohexane, n-pentane, toluene, xylene and the like, a halogenated solvent such as chloroform, dichloromethane, 1,2-dichloroethane, monochlorobenzene, o-dichlorobenzene and the like, an aprotic polar solvent such as N,N-dimethylformamide, dimethylsulfoxide, N,N-dimethylacetamide, hexamethylphosphoric triamide and the like.

The reaction temperature usually ranges from −78° C. to the boiling point of the solvent employed. The reaction time may vary depending on the types of the base and the catalyst and the temperature employed in the reaction, and usually ranges from 1 hour to 24 hours.

After the reaction, a conventional post treatment may be performed to obtain Compound (6).

If desired, the product may be further purified by a chromatography on a silica gel. The allyl halide derivative (5) as a starting material may be either an E or Z geometrical isomer, or may be a mixture thereof, or a racemate or an optically active form.

The sulfone (4) and allyl halide derivative (5) can be synthesized from geraniol or linalool.

The sulfone aldehyde derivativeof the Formula (1) is useful as an intermediate for retinal and a carotene derivative.

EXAMPLES

The present invention is further described in the following examples which are not intended to restrict the invention. In the following examples, following compounds are designated by the corresponding Roman characters.

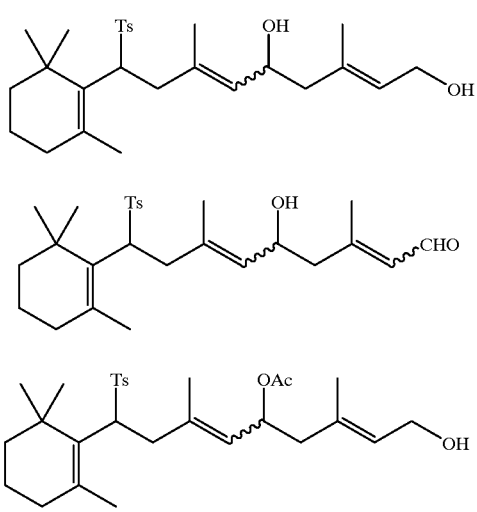

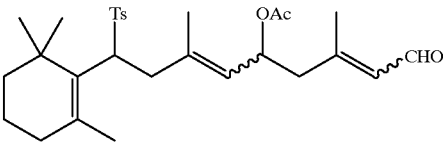

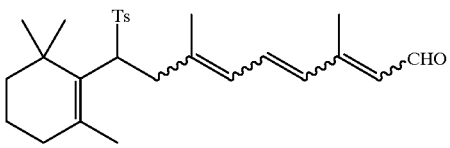

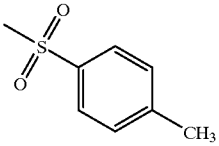

Example 1

3.3 g (7.16 mmol) of Hydroxysulfone derivative (I) were dissolved in 20 ml of dichloromethane and then 1.9 g (21.5 mmol) of manganese dioxide was added thereto. After stirring at room temperature for 3 hours followed by confirming the disappearance of the starting materials by TLC, the reaction mixture was diluted with ether. After the resulting solution was dried over anhydrous magnesium sulfate, filtered and distilled to remove the solvent to give a crude product, which was purified by a column chromatography on a silica gel to obtain the desired sulfone derivative (II) in 64% yield.

$^{1}$H-NMR $\delta$(CDCl$_3$) 0.89 (3H, s), 0.94 (3H, s), 1.45 (3H, s), 1.51 (3H, s), 1.47–1.60 (2H, m), 1.95–2.44(6H, m), 2.07 (3H, s), 2.48 (3H, s), 2.50–3.11 (2H, m) 3.89 (1H, m), 4.42 (1H, m), 5.10–5.38 (1H, m), 5.89 (1H, d, J=8 Hz), 7.33 (2H, d, J=8 Hz), 7.81 (2H, d, J=8 Hz), 9.95 (1H, d, J=8 Hz)

$^{13}$C-NMR $\delta$(CDCl$_3$) 14.1, 15.9, 16.5, 18.1, 18.9, 20.9, 21.5, 23.2, 23.3, 28.4, 28.8, 28.9, 35.8, 35.9, 39.6, 40.5, 41.1, 47.8, 48.0, 60.3, 65.5, 65.7, 66.4, 128.5, 128.6, 129.3, 130.4, 130.6, 130.8, 131.0, 134.7, 135.0, 137.8, 137.9, 138.6, 144.1 160.0, 160.1, 171.1, 190.9

Example 2

0.15 g (0.33 mmol) of Sulfone derivative (II) was dissolved in 3 ml of tetrahydrofuran and then 0.03 g (0.07 mmol) of scandium triflate was added thereto, and the resulting mixture was stirred at room temperature for 5 hours. After the reaction, the disappearance of the starting material was confirmed by TLC and the reaction mixture was filtered and the collected residue was washed with ether. The filtrate was distilled to remove the solvent to give a crude product, which was purified by a column chromatography on a silica gel to obtain the desired sulfone aldehyde derivative (V) as a mixture of E and Z isomers in 50% yield.

$^{1}$H-NMR $\delta$(CDCl$_3$) 0.89 (3H, s), 1.05 (3H, s), 1.51 (3H, s), 1.47–1.60 (4H, m) 2.07 (3H, s), 2.02–2.19 (2H, m), 2.28 (3H, s), 2.46 (3H, s), 2.65–3.19 (2H, m) 3.95 (1H, t, J=7 Hz); 5.95 (2H, m), 6.23 (1H, d, J=15 Hz), 6.76 (1H, dd, J=11, 15 Hz), 7.33 (2H, d, J=8 Hz), 7.81 (2H, d, J=8 Hz), 10.1 (1H, d, J=8 Hz)

$^{13}$C-NMR $\delta$(CDCl$_3$) 12.8, 13.0, 16.6, 18.9, 21.5, 23.2, 28.1, 28.2, 29.0, 29.2, 34.4, 34.7, 36.0, 39.6, 41.6, 65.1, 65.4, 76.5, 128.3, 128.4, 128.8, 129.1, 129.3, 129.6, 130.6, 131.4, 131.6, 132.4, 134.1, 134.3, 137.8, 138.3, 138.5, 138.9, 140.0, 143.9, 154.5, 191.0

Example 3

0.12 g (0.24 mmol) of Hydroxysulfone derivative (III) was dissolved in 10 ml of dichloromethane and then 0.06 g (0.72 mmol) of manganese dioxide was added thereto, and the resulting mixture was stirred at room temperature for 3 hours. After the reaction, the disappearance of the starting material was confirmed by TLC and the reaction mixture was filtered and the filtrate was dried over anhydrous magnesium sulfate. Then the filtered solution was distilled to remove the solvent to give a crude sulfone derivative (IV) as a mixture of E and Z isomers in 64% yield.

$^1$H-NMR δ(CDCl$_3$) 0.73–0.99 (6H, m), 1.45 (3H, s), 1.51 (3H, s), 1.38–1.60 (2H, m), 1.89–2.31 (6H, m), 2.02 (3H, s), 2.18 (3H, s), 2.45 (3H, s), 2.53–3.07 (2H, m), 3.75–3.89 (1H, m), 5.08–5.27 (1H, m), 5.58–5.92 (2H, m), 7.34 (2H, d, J=8 Hz), 7.77 (2H, d, J=8 Hz), 9.95 (1H, d, J=8 Hz).

Example 4

0.08 g (0.16 mmol) of Sulfone derivative (IV) and 2 ml of tetrahydrofuran were charged and then 0.02 g (0.016 mmol) of tetrakis(triphenylphosphine) palladium was added. The mixture was heated to 50° C. at which stirring was continued for 6 hours. After the reaction, the absence of the starting materials was confirmed by TLC and the reaction mixture was cooled, distilled to remove the solvent, whereby obtaining a crude material. The crude material thus obtained was purified by column chromatography on a silica gel to obtain the desired sulfone aldehyde derivative (V) in 37% yield.

Example 5

0.044 g (0.1 mmol) of Sulfone aldehyde (V) was dissolved in 0.5 ml of tetrahydrofuran, and 0.03 g (0.2 mmol) of DBU was added thereto. The mixture was heated to 50° C. at which stirring was continued for 4 hours. After the reaction, the reaction solution was diluted with water and the extracted with ether. The obtained organic layer was washed with 5% aqueous acetic acid solution, saturated sodium hydrogen carbonate solution, and brine in order. After being dried over anhydrous magnesium sulfate, the solvent was removed by distillation to give retinal in 80% yield.

Reference Example 1

40 g (0.204 mol) of Geranyl acetate was dissolved in n-hexane, and 17.1 g (0.071 mol) of trichloroisocyanuric acid was added portionwise and the mixture was kept at −10° C. to 0° C. for 6 hours. After the reaction, excess trichloroisocyanuric acid and a by-product, isocyanuric acid, were filtered off from the reaction system. The filtrate was washed successively with sodium hydrogen carbonate and water and dried over anhydrous magnesium sulfate, and the solvent was distilled off to obtain a crude product. The crude product thus obtained was purified by a column chromatography on a silica gel to give 6-chloro-3,7-dimethyl-2,7-octadiene-1-acetate (hereinafter referred to as Compound (a)) as a pale yellow oil in 86% yield.

Reference Example 2

To a dried four-neck flask, 6.8 g (0.17 mol) of fine powered sodium hydroxide, 2.2 g (8.5 mmol) of triphenylphosphine, 1.4 g (5.1 mmol) of tetra n-butylammonium chloride, 0.62 g (1.7 mmol) of allyl palladium chloride dimer and 100 ml of tetrahydrofuran were added. To this mixture, with stirring, a solution of 40 g (0.17 mol) of Compound (a) in 150 ml of tetrahydrofuran was added dropwise at room temperature over 1 hour. After stirring at room temperature for 3 days, the disappearance of the starting material was confirmed by TLC, and the reaction mixture was poured into water, and extracted with ether. The organic layer was washed with brine and dried over anhydrous magnesium sulfate, and then the solvent was distilled off to obtain a crude product. The crude product thus obtained was purified by a chromatography on a silica gel to obtain 3,7-dimethyl-2,5,7-octatriene-1-acetate (hereinafter referred to as Compound (b)) in 65% yield.

$^1$H-NMR δ(CDCl$_3$) 1.70 (3H, s), 1.85 (3H, s), 2.08 (3H, s), 2.81 (2H, d, J=7 Hz), 4.58 (2H, d, J=7 Hz), 4.90 (2H, s), 5.37 (1H, t, J=7 Hz), 5.61 (1H, td, J=16, 7 Hz), 6.16 (1H, d, J=16 Hz)

Reference Example 3

20.1 g (0.1 mol) of Compound (b) were dissolved in 100 ml of acetic acid, and 18.3 g (0.1 mol) of N-bromosuccinimide was added slowly thereto. The reaction mass became uniform after 10 to 15 minutes at room temperature, and after 2 hours, the disappearance of the starting material was confirmed by TLC, and then the reaction mixture was poured into water and extracted with toluene. The organic layer was dried over anhydrous magnesium sulfate, and the solvent was distilled off to give an about 1:1 mixture of 8-bromo-3,7-dimethyl-2,6-octadiene-1,5-diacetate (hereinafter referred to as Compound (c) as a E/Z mixture) and 8-bromo-3,7-dimethyl-2,5-octadiene-1,7-diacetate (hereinafter referred to as Compound (d) as a E/Z mixture) in 95% yield. The mixture thus obtained was separated to give Compound (c) as a pale yellow oil in 29% yield and Compound (d) as a pale yellow oil in 30% yield, and also the mixture thereof in 31% yield.

$^1$H-NMR δ(CDCl$_3$)
Compound (c)
1.77 (3H, s), 1.82 (3H, s), 1.98 (3H, s), 2.02 (3H, s), 2.19 (2H, m), 3.89 (2H, s), 4.55 (2H, d, J=7 Hz), 5.37 (1H, t, J=7 Hz), 5.48–5.62 (2H, m)
Compound (d)
1.65 (3H, s), 1.68 (3H, s), 2.05 (3H, s), 2.06 (3H, s), 2.78 (2H, d, J=6 Hz), 3.67 (1H, d, J=11 Hz), 3.82 (1H, d, J=11 Hz), 4.57 (2H, d, J=7 Hz), 5.35 (1H, t, J=7 Hz), 5.61–5.77 (2H, m).

Reference Example 4

0.53 g (1.8 mmol) of β-cyclogeranyl p-tolylsulfone (hereinafter referred to as Compound (e)) was dissolved in 20 ml of tetrahydrofuran, and then cooled to −60° C. At this temperature, 1.13 ml (1.8 mmol) of a hexane solution of n-butyllithium was added dropwise slowly, and the temperature was kept for 3 hours. Subsequently, 5 ml of a solution of 0.3 g (0.9 mmol) of Compound (c) in tetrahydrofuran solution was added dropwise over 1 hour. At the same temperature, the mixture was stirred for 3 hours, and the disappearance of one of the starting materials was confirmed by TLC, and the reaction mass was poured into a saturated aqueous solution of ammonium chloride and extracted with ether. The organic layer was washed with brine, and dried over anhydrous magnesium sulfate. The solvent was distilled off to obtain a crude product. The crude product thus obtained was purified by a chromatography on a silica gel to isolate 1,5-diacetoxy-3,7-dimethyl-9-(2,6,6-trimethylcyclohexen-1-yl)-9-(4-methylphenylsulfonyl)-2,6- nonadiene (hereinafter referred to as Compound (f) as a mixture of E/Z isomers and diastereomers) as a pale yellow oil in 74% yield (Rf=0.38: n-hexane/ethyl acetate=3/1).

$^1$H-NMR δ(CDCl$_3$) 0.73–1.04 (6H, m), 1.38–1.70 (6H, m), 1.39 (3H, s), 1.70 (3H, s) 2.00 (3H, s), 2.01–2.31(2H, m), 2.01 (3H, s), 2.03 (3H, s), 2.44 (3H, s), 2.66–2.95 (2H, m), 3.82–3.86 (1H, m), 4.53 (2H, d, J=7 Hz), 5.08–5.21 (1H, m), 5.34 (1H, br), 5.56 (1H, br), 7.33 (2H, d, J=8 Hz), 7.76 (2H, d, J=8 Hz)

$^{13}$C-NMR δ(CDCl$_3$) 15.1, 16.0, 16.1, 16.6, 18.8, 20.8, 20.9, 21.4, 28.2, 29.0, 35.5, 40.5, 40.8, 44.6, 60.8, 65.3, 65.5, 65.7, 68.3, 68.5, 68.8, 121.9, 127.1, 128.3, 129.4, 130.5, 130.6, 136.2, 137.1, 137.6, 137.7, 138.4, 144.0, 169.8, 170.0, 170.7

Reference Example 5

0.15 g (0.5 mmol) of Compound (e) and 0.056 g(0.5 mmol) of potassium t-butoxide butoxide were dissolved in N,N-dimethylformamide(DMF) and, cooled to −70° C., to −60° C. After stirring at the temperature for 30 min, 1 ml of a DMF solution containing 0.090 g (0.27 mmol) of Compound (c) was added dropwise thereto and stirred for 2 hours at the temperature. After confirming the disappearance of one starting material, the reation solution was poured into a saturated aqueous solution of ammonium chloride and extracted with ethyl acetate to give an organic layer. The organic layer was washed with brine. After dried over anhydrous magnesium sulfate, compound (f) was obtained as a pale yellow oil as a crude product by evaporation. The crude product was analyzed by a liquid chromatography, which showed that the yield was 78%.

Reference Example 6

0.20 g (0.37 mmol) of Compound (f) was dissolved in 5 ml of methanol and then 0.055 g (0.37 mmol) of aqueous 27% sodium hydroxide solution. After stirred for 4 hours at 25° C., disappearance of the starting material was confirmed by TLC, and then the reaction mass was poured into a saturated aqueous solution of ammonium chloride and extracted with ethyl acetate. The combined organic layer was washed with brine and dried over anhydrous magnesium sulfate. The solvent was distilled off to obtain a crude product. The crude product thus obtained was purified by a column chromatography on a silica gel to give 5-acetoxy-1-hydroxy-3,7-dimethyl-9-(2,6,6-trimethylcyclohexen-1-yl)-9-(4-methylphenylsulfonyl)-2,6-nonadiene (Hydroxysulfone derivative (III) as a mixture of E/Z isomers and diastereomers thereof) as a pale yellow oil in 37% yield.

Reference Example 7

0.20 g (0.37 mmol) of Compound (f) was dissolved in 5 ml of methanol and then 0.11 g (0.74 mmol) of aqueous 27% sodium hydroxide solution. After stirred for 4 hours at 25° C., disappearance of the starting material was confirmed by TLC, and then the reaction mass was poured into a saturated aqueous solution of ammonium chloride and extracted with ethyl acetate. The combined organic layer was washed with brine and dried over anhydrous magnesium sulfate. The solvent was distilled off to obtain a crude product. The crude product thus obtained was purified by a column chromatography on a silica gel to give 1,5-dihydroxy-3,7-dimethyl-9-(2,6,6-timethylcyclohexen-1-yl)-9-(4-methylphenylsulfonyl)-2,6-nonadiene (Hydroxysulfone derivative (I) as a mixture of E/Z isomers and diastereomers thereof) as a pale yellow oil in 95% yield.

$^1$H-NMR δ(CDCl$_3$) 0.83–1.03 (6H, m), 1.33–1.61(2H, m), 1.38 (3H, s), 1.43 (3H, s), 1.70 (3H, s), 1.90–2.18 (4H, m), 2.44 (3H, s), 2.52–2.62 (1H, m), 2.80–2.95 (1H, br), 2.95–3.13 (1H, m), 3.77–3.84 (1H, m), 3.90 (1H, t, J=7 Hz), 4.03 (2H, d, J=7 Hz), 5.33–5.36 (1H, m), 5.48–5.52 (1H, t, J=7 Hz), 7.30 (2H, d, J=8 Hz), 7.74 (2H, d, J=8 Hz).

What is claimed is:

1. A sulfone aldehyde derivative of the Formula (1):

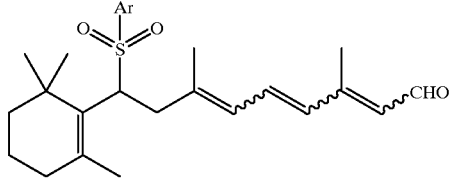

(1)

wherein Ar is a tolyl group.

2. A method for producing a sulfone aldehyde derivative of the Formula (1):

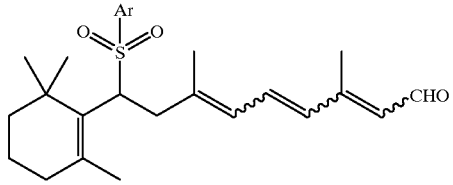

(1)

wherein Ar is an optionally substituted aryl group, which comprises contacting a sulfone derivative of Formula (2) with a palladium catalyst, whereby the OR group is removed:

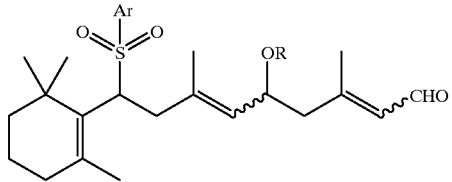

(2)

wherein Ar is as defined above in connection with Formula (1), and R is an acyl group.

3. A sulfone derivative of Formula (2):

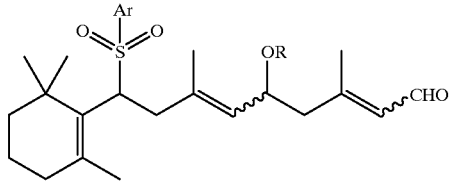

(2)

wherein Ar is an optionally substituted aryl group, and R is a hydrogen atom or an acyl group.

4. A method for producing a sulfone aldehyde derivative of the Formula (1):

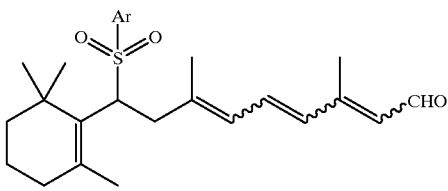

(1)

wherein Ar is an optionally substituted aryl group, which comprises subjecting a sulfone derivative of Formula (2) to a dehydration reaction in the presence of an acid catalyst, whereby the OR group is removed:

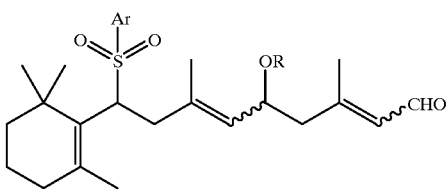

(2)

wherein Ar is as defined above in connection with Formula (1), and R is a hydrogen atom.

5. A method according to claim 2 or 4, wherein the sulfone derivative of Formula (2) is obtained by a process that comprises oxidizing a hydroxysulfone of Formula (3):

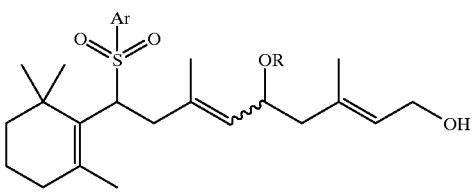

(3)

wherein Ar is an optionally substituted aryl group, and R is a hydrogen atom or an acyl group.

6. A method according to claim 5, wherein oxidizing of the hydroxysulfone derivative of Formula (3) is conducted using an oxidizing reagent selected from the group consisting of a salt or an oxide of chromium, a salt or an oxide of manganese, and an oxide of selenium.

7. A method according to claim 2 or 4, further comprising the step of contacting the sulfone aldehyde derivative of Formula (1) with a base to produce retinal.

8. A method according to claim 2 or 4, wherein Ar is a phenyl or naphthyl group optionally substituted with a group selected from a $C_1$–$C_5$ alkyl group, a $C_1$–$C_5$ alkoxy group, a halogen atom and a nitro group.

9. A method according to claim 2, wherein said acyl group is an acetyl, pivaloyl, benzoyl, or p-nitrobenzoyl group.

10. A method according to claim 9, wherein said acyl group is an acetyl group.

11. The sulfone derivative according to claim 3, wherein Ar represents a phenyl or naphthyl group optionally substituted with a group selected from a $C_1$–$C_5$ alkyl group, a $C_1$–$C_5$ alkoxy group, a halogen atom and a nitro group, and said acyl group is an acetyl, pivaloyl, benzolyl, or p-nitrobenzoyl group.

12. The sulfone derivative according to claim 3, wherein Ar represents a tolyl group and said acyl group is an acetyl group.

13. The method according to claim 2, wherein said palladium catalyst is tetrakis(triphenylphosphine)palladium.

14. A method according to claim 4, wherein said acid catalyst is a Lewis acid.

15. A method according to claim 4, wherein said acid catalyst is scandium triflate.

16. A method according to claim 5, further comprising the step of contacting the sulfone aldehyde derivative of Formula (1) with a base to produce retinal.

17. A method according to claim 5, wherein Ar is a phenyl or naphthyl group optionally substituted with a group selected from a $C_1$–$C_5$ alkyl group, a $C_1$–$C_5$ alkoxy group, a halogen atom and a nitro group.

18. A method according to claim 6, wherein Ar is a phenyl or naphthyl group optionally substituted with a group selected from a $C_1$–$C_5$ alkyl group, a $C_1$–$C_5$ alkoxy group, a halogen atom and a nitro group.

19. A method according to claim 5, wherein said acyl group is an acetyl, pivaloyl, benzoyl, or p-nitrobenzoyl group.

20. A method according to claim 6, wherein said acyl group is an acetyl, pivaloyl, benzoyl, or p-nitrobenzoyl group.

21. A method according to claim 19, wherein said acyl group is an acetyl group.

22. A method according to claim 20, wherein said acyl group is an acetyl group.

* * * * *